(12) United States Patent
Jarva

(10) Patent No.: US 9,456,793 B2
(45) Date of Patent: Oct. 4, 2016

(54) PATIENT SUPPORT FOR AN ODONTOLOGICAL X-RAY APPARATUS

(75) Inventor: Mikko Jarva, Helsinki (FI)

(73) Assignee: PLANMECA OY, Helsinki (FI)

( * ) Notice: Subject to any disclaimer, the term of this patent is extended or adjusted under 35 U.S.C. 154(b) by 157 days.

(21) Appl. No.: 13/580,450

(22) PCT Filed: Feb. 23, 2011

(86) PCT No.: PCT/FI2011/050164
§ 371 (c)(1),
(2), (4) Date: Aug. 22, 2012

(87) PCT Pub. No.: WO2011/104439
PCT Pub. Date: Sep. 1, 2011

(65) Prior Publication Data
US 2012/0321051 A1    Dec. 20, 2012

(30) Foreign Application Priority Data

Feb. 23, 2010  (FI) .................................... 20100078

(51) Int. Cl.
*A61B 6/14*    (2006.01)
*A61B 6/04*    (2006.01)

(52) U.S. Cl.
CPC .. *A61B 6/14* (2013.01); *A61B 6/04* (2013.01)

(58) Field of Classification Search
CPC .................................. A61B 6/14; A61B 6/04
See application file for complete search history.

(56) References Cited

U.S. PATENT DOCUMENTS

| | | | | |
|---|---|---|---|---|
| 3,358,141 A * | 12/1967 | Hoffmann | ............ | A61B 6/0421 128/870 |
| 3,861,666 A * | 1/1975 | Nishiyama | ............ | A61B 6/0421 128/870 |
| 3,933,154 A | 1/1976 | Cabansag | | |
| 4,030,719 A * | 6/1977 | Gabriele et al. | ................... | 5/601 |
| 4,400,820 A | 8/1983 | O'Dell | | |
| 6,526,609 B2 * | 3/2003 | Wong | .................... | A61B 6/0442 378/209 |
| 6,675,741 B2 * | 1/2004 | Remmler | ................... | A61D 3/00 119/755 |
| 7,502,441 B2 * | 3/2009 | Lebovic | ................ | A61B 6/0414 378/208 |
| 7,505,555 B2 * | 3/2009 | Hermann | ............. | A61B 6/0414 378/210 |
| 8,590,487 B1 * | 11/2013 | Goddard, Jr. | .......... | A01K 1/031 119/417 |
| 2005/0117693 A1 * | 6/2005 | Miyano | ............................ | 378/4 |
| 2006/0227938 A1 | 10/2006 | Walker et al. | | |
| 2007/0183567 A1 | 8/2007 | Rotondo et al. | | |
| 2009/0175409 A1 | 7/2009 | Stoeckl | | |

FOREIGN PATENT DOCUMENTS

| | | |
|---|---|---|
| DE | 3609260 A1 | 9/1987 |
| DE | 3627510 | 2/1988 |
| DE | 3627510 A1 * | 2/1988 |
| EP | 1491145 | 12/2004 |

(Continued)

*Primary Examiner* — Jack Berman
(74) *Attorney, Agent, or Firm* — Fay Sharpe LLP

(57) ABSTRACT

The invention relates to a patient support (17) for an odontological x-ray apparatus, which can be arranged e.g. to a patient support station (18) of the x-ray apparatus (10). The patient support (17) includes a substantially uniform, substantially curved or bendable to be curved band structure (21) substantially extending at least from one patient's temple to the other. The material and layer thickness of the band structure (21) are chosen such that the band structure (21) is soft, elastic and/or flexible and its density with respect to attenuation of x-radiation is substantially lower than that of cranial soft tissues.

19 Claims, 2 Drawing Sheets

(56) References Cited

FOREIGN PATENT DOCUMENTS

| JP | 59100403 A | 6/1984 |
| JP | 10033526 A | 2/1998 |
| KR | 20070067519 | 6/2007 |
| KR | 20070067519 A * | 6/2007 |
| WO | 03010556 A2 | 2/2003 |
| WO | 2004082481 A1 | 9/2004 |
| WO | 2007078027 A1 | 7/2007 |

* cited by examiner

PATIENT SUPPORT FOR AN ODONTOLOGICAL X-RAY APPARATUS

FIELD OF THE INVENTION

The invention relates to a patient support for an odontological x-ray apparatus according to the preamble of claim 1.

BACKGROUND OF THE INVENTION

The history of medical x-ray imaging originates approximately to the time of inventing x-radiation. Concerning more advanced ways of imaging in the dental field, for example, developing of panoramic x-ray imaging was started for over a half century ago. The advancement of digital imaging especially in the 1990s has brought digital x-ray imaging apparatuses also to the dental field. The latest step of development seen in the dental field has been the generalisation of the cone beam computed tomography apparatuses designed for three-dimensional imaging of teeth and other bones of the cranial area. Among others, the computed tomography enables imaging the cranial bones and teeth as well as soft tissues. Along with many other reasons, the generalisation of odontological computed tomography imaging has been contributed, among others, by being able to get the soft tissue of the cranial area visible better in computed tomography images than e.g. in conventional transillumination images of the cranial area.

In connection with x-ray imaging of humans, one must strive for taking care of not to expose the patient to radiation more than necessary for making a diagnosis. The size of the radiation dose can be affected, among others, by choosing the best applicable imaging technique for each situation and by developing the imaging techniques themselves. A typical problem causing extra radiation load is, however, a failure in the imaging, whereby the patient has to be re-imaged. As the imaging event can last even about twenty seconds, a typical reason for failure in the imaging is that the patient moves or stirs during the imaging process.

The field of odontology commonly employs x-ray apparatuses where the patient sits or stands positioned in a patient support means during the imaging. Commonly found structures in such support means include e.g. a jaw support, a bite support, support bars positioned on the patient's temples which mainly provide point-like support sideways, and a forehead support. As examples of prior-art patient support arrangements the application publications US 2006/0227938, US 2007/0183567 and DE 3609260 can be mentioned.

For instance, in odontological panoramic and cone-beam computed tomography imagings where the imaging means rotate around the patient's head, the imaging event typically lasts of the order of 10-20 seconds. A large-size C-arm turning around the head in front of the patient's face can easily frighten the patient and, also otherwise due to the duration of the imaging event, the patient's head may tend to move from its place or turn during the exposure.

Many prior-art patient support arrangements have not necessarily been aimed at actually assisting the head staying at in place in other than one or some specific directions for the most, their use as supports for patients of different sizes can be challenging and/or they may feel uncomfortable for the patient. Discomfort can be the result of e.g. the construction of the support structure together with the materials used in it. At the same time, the material used in the support structures is often such that, although it typically absorbs x-radiation only a little and thus is no problem for the x-ray imaging of the cranial bones, its density with respect to attenuation of x-radiation can still be of such order which causes problems considering imaging of cranial soft tissues.

BRIEF DESCRIPTION OF INVENTION

The object of the invention is to provide a patient support for an odontological x-ray apparatus which can conform without special arrangements to be the support for a head of more than one specific size and which is implemented such that the patient support is not visible or it is easily removable e.g. from computed tomography images of the cranial area, in which also the soft tissue is wished to be seen.

The characteristics of the invention are described in the accompanying patent claims. The invention with its preferable embodiments not only provides support to make it easier for the patient to keep his/her head stationary during an exposure but it even prevents moving the head forward and/or backward. Furthermore, the support hinders turning and sideways motions of the head during exposure and it further offers quite a good support even without simultaneously employing some prior-art jaw and/or bite support.

Next, the invention and its preferable embodiments will be described in more detail and with reference to the enclosed figures.

DETAILED DESCRIPTION OF INVENTION

Figure 1:
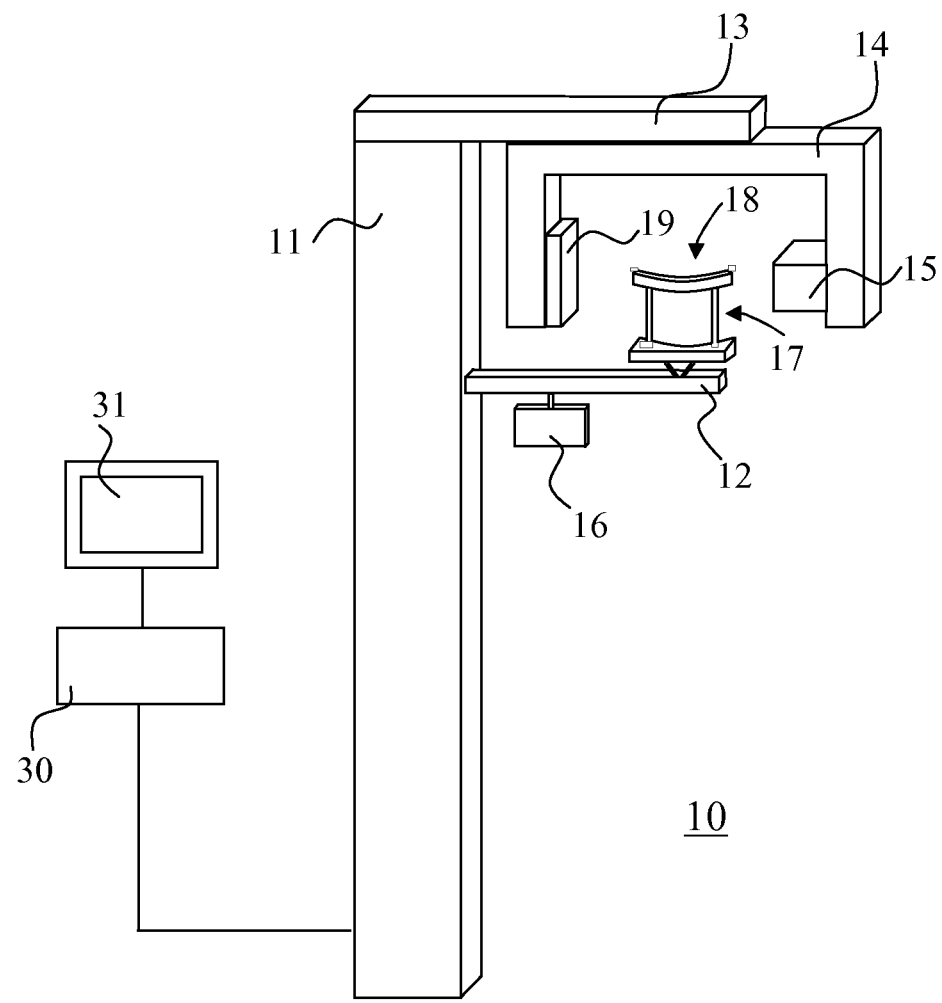
FIG. 1 shows a typical odontological x-ray imaging apparatus its basic structure including a base construction, an arm part supporting imaging means and a patient support station.

FIG. 1 shows an x-ray imaging apparatus (10) including a vertical base construction (11) from which horizontally extend a structure (12) supporting patient support means (17) and an arm part (13) which supports a structure supporting the imaging means, an arm part (14). To the arm part supporting the imaging means (14) are arranged at a distance from each other an x-ray source (15) and a receiver of x-ray image information (19), which have been located to the apparatus with respect to the patient support means (17) such that to the apparatus is formed an imaging station (18) which is positioned between the x-ray source (15) and the receiver means of x-ray image information (19) such that a beam produced by the x-ray source (15) is alignable to go through said imaging station (18) towards the receiver means of x-ray image information (19). The arm part supporting the imaging means (14) is arranged rotatable, and also its location with respect to the structure supporting it (13) and/or the patient support station (18) may be arranged changeable. The apparatus includes a control means, of which FIG. 1 shows a control panel (16) located into connection with the arm (12) supporting the patient support means. The apparatus (10) can be arranged connected to a computer (30) via a cable and the computer can be arranged with a means for processing image information produced by the apparatus and a display (31) on which images can be shown.

Figure 2:
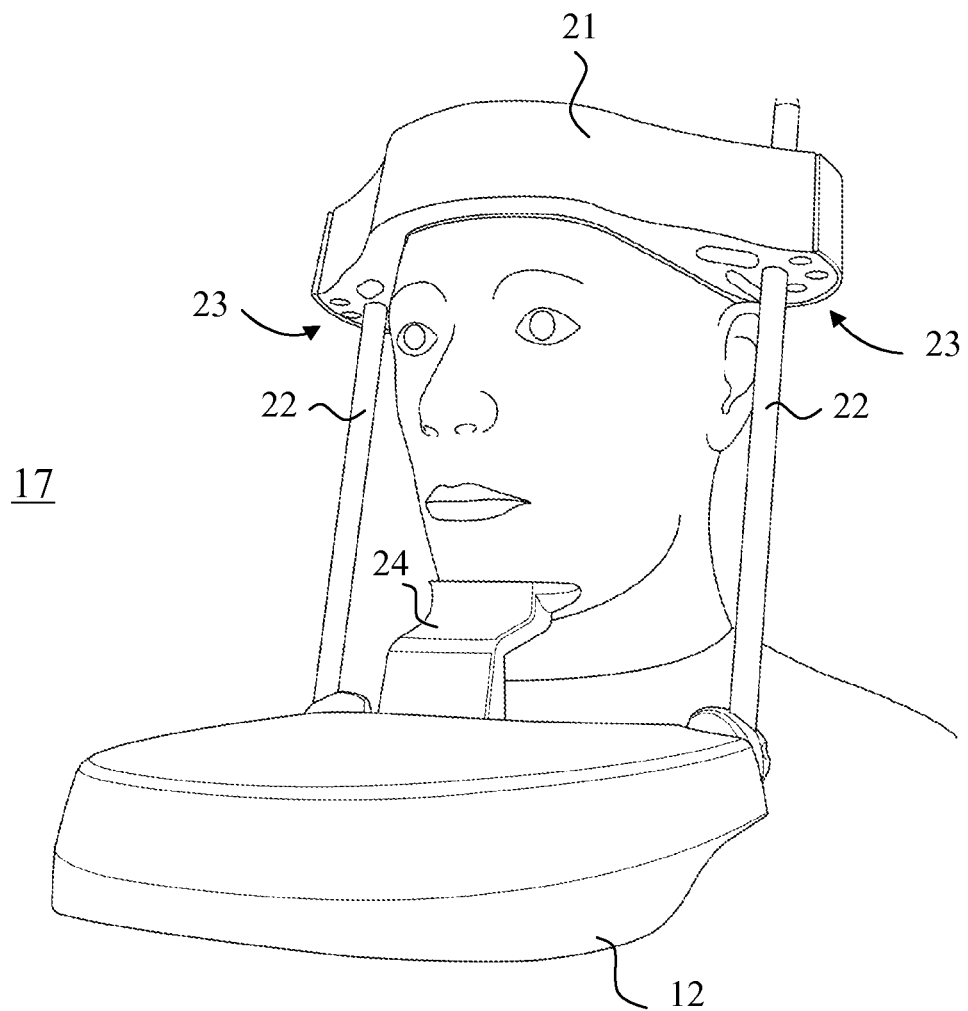
FIG. 2 shows an embodiment of a patient support according to the invention.

FIG. 2 shows a patient support (17) according to the invention. The patient support (17) comprises a band structure (21) conforming to the shape of the patient's head. The band structure (21) is supported through two vertical supports (22) to the structure (12) supporting the patient support. In the embodiment according to FIG. 2, the patient support means (17) is also arranged with a jaw support (23) which can be detachably attached to the structure (12) supporting the patient support (17).

In the embodiment according to FIG. 2, the vertical supports (22) are substantially straight bars and, in the areas of the band structure (21) the side wall of which gets positioned against the temples, holes (23) are arranged for the vertical supports (22) closely corresponding to the diameter of the vertical supports (22). The shape of the vertical supports (22) can be straight or some other, such as curved, and their number can also be arranged to be some other than two. The holes (23) are preferably trough-holes or at least so deep that a vertical degree of freedom of motion is provided to adjust the height position of the band structure (21). One or more holes (23) can also be implemented which are open in the direction of the edge of the band structure (21) such that the vertical support (22) can be placed in the hole (23) besides from the direction of the central axis of the hole (23) also from the side of the band structure (21). To improve the adjustability and suitability of the patient support (17) for various patients, the band structure (21) may be arranged with several holes (23) for the vertical supports (22) at different locations. It is also possible to integrate or arrange attachable to the band structure (21) a strap which can be set to go round the patient's skull from the opposite side of the skull to the section which the band structure (21) supports (and which strap is thus not shown in FIG. 2). The attachment of such a strap to the band structure (21) can also utilise the holes (23) of the band structure (21) primarily arranged for the vertical supports (22). The material and thickness of the band structure (21) are chosen such that it can, as soft, elastic and/or flexible, rest on a wide area on the surface of heads of different sizes and shapes. By choosing the holes (23) used in the attachment of the band structure (21) along with the elastic structure of the band structure (21), it is possible to affect the supporting properties of the band structure (21) and also to implement the support asymmetrically. The support properties of the elastic band structure (21) can also be affected by arranging holes or cuts of desired sizes at desired locations thereof. When the pressing force of the band can be adjusted, it enhances the possibility to use the band also without the jaw support (24) shown in FIG. 2, when required.

Medical x-ray imaging typically employs acceleration voltage in the range of the order of 50-150 kV. A Hounsfield unit (10 is a variable representing density of the object with respect to attenuation of x-radiation. According to the definition, its value for air is −1000 and for water zero. The band structure (21) of the patient support (17) can be implemented according to the invention such that its density with respect to the attenuation of x-radiation is substantially lower than that of cranial tissues. With realistic material thicknesses of the band structure (21), this means e.g. a material the Hounsfield unit of which is of the order of at least 100 units lower than the HU of the cranial soft tissues, preferably at least 300 units lower. Depending on the imaging arrangement, the HU of the cranial soft tissues is typically of the order of zero+/−100 units. Examples of suitable materials are cellular plastics and other porous materials and/or ones containing air bubbles. The band structure (21) thus comprises according to the invention a material layer or it consists of a material the Hounsfield unit of which is of the order of at least 100 units lower than the HU of the cranial soft tissues, preferably at least 300 units lower. It is possible to arrange to the band structure (21) various holes both for the above-mentioned adjustment purpose and for decreasing radiation absorption of the construction. The band structure (21) can also be implemented e.g. as a suitably shaped air cushion or as one to be filled into a suitable shape. Preferably, also the vertical supports (22) included in the patient support (17) are manufactured of a material absorbing only a little x-radiation, such as carbon fibre.

The structure shown in FIG. 2 for attaching the band structure (21) to the patient support structure (17) also enables the use of the band structure (21) the other way around, for supporting the neck. Such support for a patient may be applied e.g. when, in addition to the x-ray imaging means, to the x-ray apparatus is arranged a means for photographing the patient's face. Then, it is possible e.g. to implement facial photographing in the same set of coordinates and even in connection with the same imaging event as the x-ray imaging such that no forehead nor jaw support is visible in the photograph or photographs. The embodiment of the invention shown in FIG. 2 also enables e.g. simultaneous use of two band structures (21) such that the first is used as the support on the forehead side and the other on the neck side. The band structure (21) can also be implemented as a structure extending totally around the skull.

The curved shape of the band structure (21) is implemented according to one preferable embodiment of the invention such that thickness of the material layer of the band structure (21) is not constant but it includes one or more thinner sections. Thus, when adjusting the shape of the band structure (21) its curvature changes primarily in these thinner sections. When the material of the band structure (21) is elastic, its manufacture can be implemented from the viewpoint of economical manufacturing technique and also such that the band structure (21) is not readily curved but it bends to its curved shape when positioning the band structure (21) to the patient support structure (17). One preferable way to implement such a band structure (21) is to arrange the sections of the band structure (21) positioned in the area between the forehead and the temples thinner than the ends of the band structure (21) and/or the point of the band structure (21) getting positioned in the middle of the forehead, whereby the band structure (21) bends mostly at those thinner sections. The ends of the band structure (21) extending to the temples can be arranged thicker than its middle area to better enable implementation of several attaching holes for the support bars (22) and/or other adjustment holes (23) in the structure. The band structure (21), especially its surface getting positioned against the patient's skin, can be covered or coated with a thin material layer suitable for the purpose.

The patient support (17) according to the invention can be considered to be arranged either as a fixed part of the imaging apparatus according to FIG. 2 or to be positioned into functional connection with the patient support station (18) of the imaging apparatus. The band structure (21) does not necessarily have to be precisely like the one shown in FIG. 2 but it is advantageous and substantial to arrange it to support on the patient's head over an area substantially larger than the area of the temples.

The invention claimed is:

1. An odontological x-ray apparatus comprising an x-ray source and a means for receiving x-ray imaging information, said x-ray apparatus further comprising a patient support arranged to a patient support station of said x-ray apparatus or to be positioned into functional connection with said patient support station, said patient support station being configured to receive a standing or sitting patient, said x-ray source and means for receiving x-ray images being configured for at least computed tomography and arranged to the apparatus with respect to said patient support station such that the x-ray source and the receiver means of x-ray imaging information are positionable on opposite sides of the patient support station and rotatable around the patient support station such that three-dimensional imaging of at least one cranial anatomy can be performed, characterized in that the patient support includes a substantially uniform, substantially curved or bendable to be curved band structure for a forehead of a patient, which extends substantially at least from one patient's temple to the other, and includes a plurality of holes, the material and layer thickness of which band structure being chosen such that the band structure is soft, elastic and flexible and its density with respect to attenuation of x-radiation is substantially lower than that of cranial soft tissues, and at least two support bars connected or connectable to said holes arranged to said band structure, and wherein said plurality of holes comprise through holes facilitating adjustment of a height position of the band structure relative to said support bars, and wherein said holes are configured to allow attachment of the band structure to said at least two support bars in an asymmetrical configuration.

2. The patient support according to claim 1, characterized in that said band structure comprises a material layer or it consists of a material the Hounsfield unit (HU) of which is at least 100 units lower than that of the cranial soft tissue.

3. The patient support according to claim 1, characterized in that said band structure comprises a material layer or it consists of a material the Hounsfield unit (HU) of which is at least 300 units lower than that of the cranial soft tissue.

4. The patient support according to claim 1, characterized in that on the top and/or bottom surface of the band structure at least one hole is closed and/or open in the direction of an edge of the band structure.

5. The patient support according to claim 1, characterized in that said holes are arranged to locate in the areas of the band structure the side wall of which gets positioned against the temples.

6. The patient support according to claim 1, characterized in that the thickness of the material layer of the band structure is not constant but it includes one or more thinner sections.

7. The band structure according to claim 6, characterized in that the sections of the band structure which get positioned in the area between the forehead and the temples are arranged thinner than the ends of the band structure and/or the point of the band structure which gets positioned at the middle of the forehead.

8. The patient support according to claim 1, characterized in that the band structure is arranged to extend around the whole skull or a strap is arranged to be attached to the band structure to extend round the opposite side of the skull than that part of the skull the band structure supports.

9. The patient support according to claim 1, characterized in that the band structure is arranged to support on the patient's head over an area substantially larger than the area of the temples.

10. The patient support according to claim 8, including the strap and wherein the strap is attached to at least one hole.

11. The patient support according to claim 1, wherein at least one support bar is comprised of carbon fiber.

12. The patient support according to claim 1, wherein the curved band structure includes a first component receiving the patient's forehead and a second substantially equivalently configured component receiving the backside of the patient's head.

13. The patient support according to claim 1 wherein at least one hole is open to an edge of the band structure.

14. A patient support according to claim 1 wherein said band structure includes a surface coating.

15. The patient support according to claim 1 wherein the material of the band structure is selected from cellular plastic, porous and air bubble containing materials.

16. The patient support of claim 1 wherein the cranial anatomy of the patient is retained only by a jaw support and said band structure.

17. A patient support for an odontological x-ray apparatus, which patient support is arranged to a patient support station of said x-ray apparatus or to be positioned into functional connection with said patient support station, imaging means of which x-ray apparatus include at least an x-ray source and a means for receiving x-ray imaging information, which are configured for at least computed tomography and are arranged to the apparatus with respect to said patient support station such that the x-ray source and the receiver means of x-ray imaging information are positionable on opposite sides of the patient support station and rotatable around the patient support station such that three-dimensional imaging of at least one cranial anatomy can be performed, characterized in that the patient support includes a substantially uniform, substantially curved or bendable to be curved band structure for a forehead of a patient, which extends substantially at least from one patient's temple to the other, and includes a plurality of holes, at least two of said holes being comprised of different sizes and/or shapes, the material and layer thickness of which band structure being chosen such that the band structure is soft, elastic and/or flexible and its density with respect to attenuation of x-radiation is substantially lower than that of cranial soft tissues, and at least two support bars connected or connectable to said holes arranged to said band structure.

18. The patient support according to claim 17, wherein at least one of said holes comprises an elongated cut.

19. A patient support for an odontological x-ray apparatus, which patient support is arranged to a patient support station of said x-ray apparatus or to be positioned into functional connection with said patient support station, imaging means of which x-ray apparatus include at least an x-ray source and a means for receiving x-ray imaging information, which are configured for at least computed tomography and are arranged to the apparatus with respect to said patient support station such that the x-ray source and the receiver means of x-ray imaging information are positionable on opposite sides of the patient support station and rotatable around the patient support station such that three-dimensional imaging of at least one cranial anatomy can be performed, characterized in that the patient support includes a substantially uniform, substantially curved or bendable to be curved band structure for a forehead of a patient, which extends substantially at least from one patient's temple to the other, wherein said sections of the band which get positioned in the area between the forehead and the temples are arranged thinner than the ends of the band structure and thinner than the point of the band structure which gets positioned in the middle of the forehead, the material and layer thickness of which band structure being chosen such that the band structure is soft, elastic and/or flexible and its density with respect to attenuation of x-radiation is substantially lower than that of cranial soft tissues, and at least two support bars connected or connectable to said holes arranged to said band structure.

* * * * *